(12) United States Patent
Pinney et al.

(10) Patent No.: US 7,456,214 B2
(45) Date of Patent: Nov. 25, 2008

(54) CHROMENE-CONTAINING COMPOUNDS WITH ANTI-TUBULIN AND VASCULAR TARGETING ACTIVITY

(75) Inventors: Kevin G. Pinney, Woodway, TX (US); Phyllis Arthasary, Waco, TX (US); Anupama Shirali, Hamden, CT (US); Klaus Edvardsen, Lund (SE); David J. Chaplin, Watlington (GB)

(73) Assignees: Baylor University, Waco, TX (US); OXiGENE, Inc., Waltham, MA (US)

( * ) Notice: Subject to any disclaimer, the term of this patent is extended or adjusted under 35 U.S.C. 154(b) by 254 days.

(21) Appl. No.: 10/851,445

(22) Filed: May 21, 2004

(65) Prior Publication Data
US 2005/0245490 A1  Nov. 3, 2005

(51) Int. Cl.
| | | |
|---|---|---|
| A61K 31/665 | (2006.01) | |
| A61K 31/352 | (2006.01) | |
| C07D 311/58 | (2006.01) | |
| C07D 311/64 | (2006.01) | |
| C07F 9/12 | (2006.01) | |

(52) U.S. Cl. .................. 514/456; 549/220; 549/405; 514/100

(58) Field of Classification Search .................. 549/218, 549/399, 400, 405, 404; 514/456
See application file for complete search history.

(56) References Cited

U.S. PATENT DOCUMENTS

| | | | |
|---|---|---|---|
| 4,133,814 A | 1/1979 | Jones et al. | 260/326.55 |
| 4,656,187 A | 4/1987 | Black et al. | 514/422 |
| 4,737,517 A | 4/1988 | della Valle et al. | 514/457 |
| 5,532,382 A | 7/1996 | Carlson et al. | 549/57 |
| 5,596,106 A | 1/1997 | Cullinan et al. | 549/57 |
| 5,886,025 A | 3/1999 | Pinney | 514/443 |
| 5,952,350 A | 9/1999 | Cullinan et al. | 514/319 |
| 5,958,916 A | 9/1999 | Bryant et al. | 514/212 |
| 6,162,930 A | 12/2000 | Pinney et al. | 549/57 |
| 6,277,879 B1 | 8/2001 | Xu et al. | 514/453 |
| 6,291,456 B1 | 9/2001 | Stein et al. | 514/233.5 |
| 6,331,562 B1 | 12/2001 | Bhagwat et al. | 514/457 |
| 6,350,777 B2 | 2/2002 | Pinney et al. | 514/469 |
| 6,573,219 B1 | 6/2003 | Linker et al. | 504/229 |
| 6,593,374 B2 | 7/2003 | Pinney et al. | 514/721 |
| 2002/0161245 A1 | 10/2002 | Huang | 549/401 |
| 2003/0176494 A1 | 9/2003 | Xu et al. | 514/455 |

FOREIGN PATENT DOCUMENTS

| | | |
|---|---|---|
| EP | 1 028 110 A1 | 8/2000 |
| JP | 63-213503 | * 9/1988 |
| WO | WO 96/40137 | 12/1996 |
| WO | WO 98/39323 | 9/1998 |
| WO | WO 99/34788 | 7/1999 |
| WO | WO 01/19794 A2 | 3/2001 |
| WO | WO 02/060872 A1 | 8/2001 |
| WO | WO 01/68654 A2 | 9/2001 |
| WO | WO 01/77093 A1 | 10/2001 |
| WO | WO 01/79180 A2 | 10/2001 |
| WO | WO 01/81288 A1 | 11/2001 |
| WO | WO 03/096982 A2 | 11/2003 |
| WO | WO 03/105842 A1 | 12/2003 |

OTHER PUBLICATIONS

Bellassoued-Fargeau et al. J. Heterocyclic Chem., 22:45-46 (1985).*
Koga, H et al 'Preparation of benzopyran derivatives as potassium channel activators' CA 117:7803 (1992).*
O'Donnell RWH et al 'Synthesis of rotenone and its derivatives. IX.' CA 30:36771 (1936).*
Butenandt, A et al 'Vegetable, fish and insect poinons. IV> Constituents of varieties of Derris and Tephrosia. [Constitution of deguelin, tephrosin and toxicarol]' CA 26:36536 (1932).*
Chemical Abstracts 123:270364, RN 169227-65-0.*
Bailly, et al., J. Med. Chem., 46:5437-5444 (2003).
Boyd, et al., Drug Dev. Res., 34:91-109 (1995).
Churcher, et al., J. Am. Chem. Soc., 120:13350-10358 (1998).
Clive, et al., J. Am. Chem. Soc., 120:10332-10349 (1998).
Cushman, et al., J. Med. Chem., 38:2041-2049 (1995).
Cushman, et al., J. Med. Chem., 40:2323-2334 (1997).
D'Amato, et al., Proc. Natl. Acad. Sci. USA, 91:3964-3968 (1994).
Flynn, et al., Organic Lett., 3(5):651-654 (2001).
Grese, et al., J. Med. Chem., 40: 146-167 (1997).
Hamel, et al., Biochem., 35(4):1304-1310 (1996).
Jones, et al., J. Med. Chem., 27:1057-1066 (1984).
Mullica, et al., J. Chem. Cryst., 28(4):289-295 (1998).
Myers, et al., J. Am. Chem. Soc., 119(26):6072-6094 (1997).
Palkowitz, et al., J. Med. Chem., 40(10):1407-1416 (1997).
Pinney, et al., Bioorg. Med. Chem. Lett., 9:1081-1086 (1999).

* cited by examiner

Primary Examiner—Bernard Dentz

(57) ABSTRACT

Chrome compounds have been discovered which demonstrate impressive cytotoxicity as well as a remarkable ability to inhibit tubulin polymerization. Such compounds as well as related derivatives are excellent clinical candidates for the treatment of cancer in humans. In addition, certain of these ligands, as pro-drugs, may well prove to be tumor selective vascular targeting chemotherapeutic agents or to have vascular targeting activity resulting in the selective prevention and/or destruction of nonmalignant proliferating vasculature.

20 Claims, 1 Drawing Sheet

CHROMENE-CONTAINING COMPOUNDS WITH ANTI-TUBULIN AND VASCULAR TARGETING ACTIVITY

FIELD OF THE INVENTION

Chromene compounds have been discovered which demonstrate impressive cytotoxicity as well as a remarkable ability to inhibit tubulin polymerization. Such compounds as well as related derivatives are excellent clinical candidates for the treatment of cancer in humans. In addition, certain of these ligands, as pro-drugs, may well prove to be tumor selective vascular targeting chemotherapeutic agents or to have vascular targeting activity resulting in the selective prevention and/or destruction of nonmalignant proliferating vasculature.

BACKGROUND OF THE INVENTION

The cytoskeletal protein tubulin is among the most attractive therapeutic drug targets for the treatment of solid tumors. A particularly successful class of chemotherapeutics mediates its anti-tumor effect through a direct binding interaction with tubulin. This clinically promising class of therapeutics, called tubulin binding agents or Anti-tubulin agents, exhibit potent tumor cell cytotoxicity by efficiently inhibiting the assembly of αβ-tubulin heterodimers into the microtubule structures that are required to facilitate mitotic cell division (Li & Sham, Expert Opin. Ther. Patents., 2002).

Currently, the most widely recognized and clinically useful anti-tubulin chemotherapeutics agents are the Vinca Alkaloids, such as Vinblastine and Vincristine (Owellen et al, *Cancer Res.*, 1976) along with Taxanes such as Taxol (Schiff et al, *Nature*, 1979). Additionally, natural products such as Rhizoxin (Rao et al, *Tetrahedron Lett.*, 1992), the Combretastatins (Pettit et al, *Can. J. Chem.*, 1982), Curacin A (Gerwick et al, *J. Org. Chem.*, 1994), Podophyllotoxin (Coretese et al, *J. Biol. Chem.*, 1977), Epothilones A and B (Nicolau et al., *Nature*, 1997), Dolastatin-10 (Pettit et al, *J. Am. Chem. Soc.*, 1987), and Welwistatin (Zhang et al, *Molecular Pharmacology*, 1996), as well as certain synthetic analogues including Phenstatin (Pettit G R et al., *J. Med. Chem.*, 1998), 2-styrylquinazolin-4(3H)-ones ("SQOs", Jiang et al, *J. Med. Chem.*, 1990), and highly oxygenated derivatives of cis- and trans-stilbene and dihydrostilbene (Cushman et al, *J. Med. Chem.*, 1991) are all known to mediate tumor cytotoxic activity through a mode of action that includes tubulin binding and subsequent inhibition of mitosis.

Normally, during the metaphase of cell mitosis, the nuclear membrane has broken down and tubulin is able to form centrosomes (also called microtubule organizing centers) that facilitate the formation of the microtubule spindle apparatus to which the dividing chromosomes become attached. Subsequent assembly and disassembly of the spindle apparatus mitigates the separation of the daughter chromosomes during anaphase such that each daughter cell contains a full complement of chromosomes. As antiproliferatives or antimitotic agents, tubulin binding agents exploit the relatively rapid mitosis that occurs in proliferating tumor cells. By binding to tubulin and inhibiting the formation of the spindle apparatus in a tumor cell, the tubulin binding agent can cause significant tumor cell cytotoxicity with relatively minor effects on the slowly dividing normal cells of the patient.

The exact nature of tubulin binding site interactions remains largely unknown, and they definitely vary between each class of tubulin binding agent. Photoaffinity labeling and other binding site elucidation techniques have identified three key binding sites on tubulin: 1) the Colchicine site (Williams et al, *J. Biol. Chem.*, 19851); 2) the Vinca Alkaloid site (Safa et al, *Biochemistry*, 1987); and 3) a site on the polymerized microtubule to which taxol binds (Lin et al, *Biochemistry*, 1989). An important aspect of this work requires a detailed understanding, at the molecular level, of the "small molecule" binding domain of both the α and β subunits of tubulin. The tertiary structure of the α,β tubulin heterodimer was reported in 1998 by Downing and co-workers at a resolution of 3.7 Å using a technique known as electron crystallography (Nogales et al, *Nature*, 1998). This brilliant accomplishment culminated decades of work directed toward the elucidation of this structure and should facilitate the identification of small molecule binding sites, such as the colchicine site, using techniques such as photoaffinity and chemical affinity labeling (Chavan et al, *Bioconjugate Chem.*, 1993; Hahn et al, *Photochem. Photobiol.*, 1992).

Further significance is given to new drugs that bind to the colchicine site since it has recently been shown that many tubulin binding agents also demonstrate activity against malignant proliferating tumor vasculature, as opposed to the tumor itself. Antivascular chemotherapy is an emerging area of cancer chemotherapy which centers on the development of drugs that target the proliferation of the vasculature that supports tumor growth. Much of the research in anti-vascular cancer therapy has focused on understanding the process of new blood vessel formation, known as angiogenesis, and identifying anti-angiogenic agents which inhibit the formation of new blood vessels. Angiogenesis is characterized by the proliferation of tumor endothelial cells and generation of new vasculature to support the growth of a tumor. This growth is stimulated by certain growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered over a period of months to years in order to produce the desired effect.

Vascular Targeting Agents ("VTAs") or vascular damaging agents, are a separate class of antivascular chemotherapeutics. In contrast to anti-angiogenic drugs which disrupt the new microvessel formation of developing tumors, VTAs attack solid tumors by selectively targeting the established tumor vasculature and causing extensive shutdown of tumor blood flow. A single dose of a VTA can cause a rapid and selective shutdown of the tumor neovasculature within a period of minutes to hours, leading eventually to tumor necrosis by induction of hypoxia and nutrient depletion. This vascular-mediated cytotoxic mechanism of VTA action is quite divorced from that of anti-angiogenic agents, which inhibit the formation of new tumor vascularization rather than interfering with the existing tumor vasculature. Other agents have been known to disrupt tumor vasculature, but differ in that they also manifest substantial normal tissue toxicity at their maximum tolerated dose. In contrast, genuine VTAs retain their vascular shutdown activity at a fraction of their maximum tolerated dose. It is thought that Tubulin-binding VTAs selectively destabilize the microtubule cytoskeleton of tumor endothelial cells, causing a profound alteration in the shape of the cell which ultimately leads to occlusion of the tumor blood vessel and shutdown of blood flow to the tumor (Kanthou et al, *Blood*, 2002).

Combretastatin A4 phosphate prodrug (CA4P) is one of the leading new candidates from among a relatively small collection of known world compounds with vascular targeting activity (U.S. Pat. No. 5,561,122; Chaplin et al, *Anticancer Res.*, 1999; Tozer et al, *Cancer Res.*, 1999; Pettit and Rhodes, *Anti-Cancer Drug Des.*, 1998; Iyer et al, *Cancer Res.*, 1998; Dark et al, *Cancer Res.*, 1997). Its parent phenol compound, Combretastatin A-4 (CA4) was discovered by Professor George R. Pettit (Arizona State University) as an isolate from South African bush willow (*Combretum caffrum*) in the 1970s. CA4 is a potent inhibitor of tubulin polymerization and binds to the colchicine site on β-tubulin. Interestingly, CA4 itself does not demonstrate destruction of tumor vasculature, while CA4P is very active in terms of tumor vasculature destruction. Therefore, the phosphate ester portion of CA4P undergoes dephosphorylation to reveal the potent tubulin binder CA4 that destroys the tumor cell through an inhibition of tubulin polymerization.

CA4P is currently the lead drug in a group of tubulin-binding VTAs under clinical development. Other tubulin binding VTAs that have been discovered include the Colchicinoid ZD6126 (Davis et al., *Cancer Research*, 2002) and the Combretastatin analog AVE8032 (Lejeune et al, *Proceedings of the AACR.*, 2002).

An aggressive chemotherapeutic strategy for the treatment and maintenance of solid tumor cancers continues to rely on the development of architecturally new and biologically more potent compounds. The present invention addresses this urgent need by providing a structurally novel class of tubulin binding agent compositions with potent antiproliferative activity and tumor cell cytotoxicity. In addition, the present invention provides the important discovery that corresponding prodrug constructs of these agents have selective effects on the tumor vasculature that are independent of any antimitotic effect on the cells of the tumor. These agents are capable of selectively shutting down the flow of blood to a tumor and causing secondary tumor cell death. Thus the present compositions have expanded clinical utility over known tubulin binding agents.

SUMMARY OF THE INVENTION

The present invention relates to a discovery of chromene compounds which function as tubulin binding agents capable of inhibiting tubulin assembly and tumor cell proliferation. These chromene compounds result from the judicious combination of a non-tubulin binding molecular template, suitably modified with structural features such as hydroxyl moieties and arylalkoxy groups.

In a first general aspect, the present invention provides a chromene compound of the following general formula I:

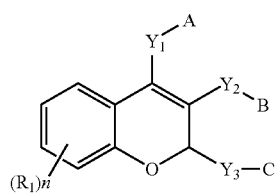

wherein $R_1$ is independently selected from H, OH, nitro, amine, lower alkyl, lower alkoxy, phosphate, or halogen;

n is 0, 1, 2, 3, or 4;

$Y_1$, $Y_2$ and $Y_3$ are optionally a covalent bond, —CO—, —O—, —S—, —CH$_2$—, or —CH$_2$O—; and A, B, and C are optionally H, OH, nitro, amine, phosphate, halogen or optionally substituted alkyl, alkoxy, cycloalkyl, aryl, or heteroaryl.

In a more specific aspect, the invention provides 3-aroyl chromenes of the following structural formula Ia:

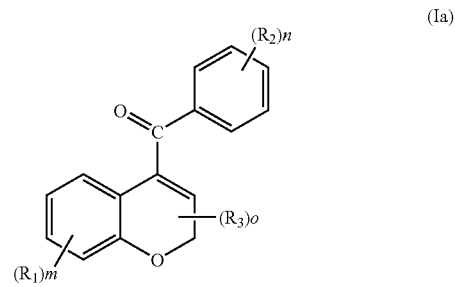

wherein $R_1$, $R_2$, and $R_3$ are independently selected from H, OH, nitro, amine, lower alkyl, lower alkoxy, phosphate, or halogen;

m is 0, 1, 2, 3, or 4;

n is 0, 1, 2, 3, 4, or 5; and o is 0, 1, or 2.

n is desirably 1, 2 or 3. In an embodiment, n is 3 and $R_2$ is lower alkoxy, e.g., methoxy. m is desirably 1, or 2. In an embodiment, $R_1$ is lower alkoxy, e.g., methoxy, or hydroxyl.

The compounds of the invention also include prodrug forms of the compound, e.g., phosphate prodrugs.

In a second general aspect, the invention contemplates methods of contacting a tubulin-containing system with an effective amount of a compound of Formula I. Methods are also provided for treating a warm-blooded animal afflicted with a neoplastic disease comprising administering an effective amount of compound capable of inhibiting the proliferation of the neoplastic disease. In a preferred embodiment, the antiproliferative effect has the direct result of causing tumor cell cytotoxicity due to inhibition of mitosis.

In a third aspect, the invention broadly contemplates the provision of a method for treating a warm-blooded animal having a vascular proliferative disorder comprising administering an effective amount of a compound of the present invention to achieve targeted vascular toxicity at a locality of proliferating vasculature, wherein the proliferating vasculature is malignant or nonmalignant.

In yet another aspect, the invention broadly contemplates the provision of a method for administering an effective amount of a compound of the present invention to selectively reduce the flow of blood to at least a portion of a neoplastic region, thereby causing substantial necrosis of tissue in the neoplastic region without substantial necrosis of tissue in adjoining regions. In a preferred embodiment, the effect of reduced tumor blood flow is reversible so that normal tumor blood flow is restored following cessation of treatment.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

Figure 1:
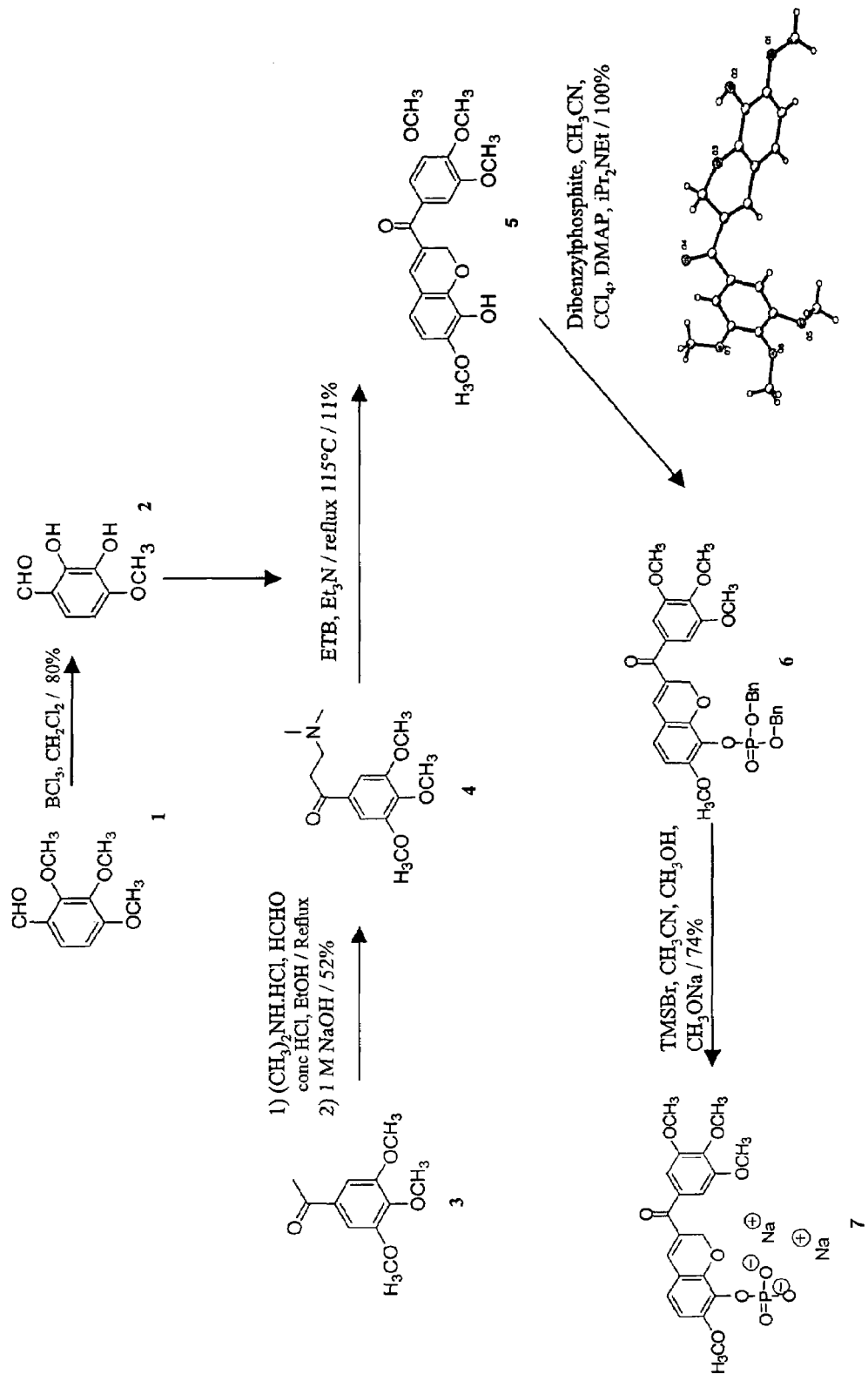
FIG. 1 depicts a route for the synthesis of an exemplary chromene of the invention.

We have developed a working hypothesis suggesting that the discovery of new anti-mitotic agents may result from the judicious combination of a molecular template (scaffold) that interacts with estrogen receptor (ER), and can be suitably modified with structural features deemed imperative for tubulin binding (i.e. hydroxyl, arylalkoxy groups, certain halogen substitutions, etc.). In particular, the methoxy aryl functionality seems important for increased interaction at the colchicine binding site in certain analogs (Shirai et al., *Biomedical Chem. Lett.* 1994). Upon formulation of this hypothesis concerning ER molecular templates, our initial design and synthesis efforts centered on benzo[b]thiophene ligands containing structural motifs reminiscent of raloxifene, the selective estrogen receptor modulator (SERM) developed by Eli Lilly and Co. (Jones et al, *J. Med. Chem.* 1984; Grese et al, *J. Med. Chem.*, 1997; Palkowitz et al., *J. Med. Chem.*, 1997), as well the colchicine and combretastatin tubulin binding agents.

The design premise that molecular skeletons of traditional estrogen receptor (ER) binding compounds can be modified with structural motifs reminiscent of colchicine and combretastatin A4 to produce especially inhibitors of tubulin polymerization has been validated by our preparation of very active benzo[b]thiophene, benzo[b]furan, and indole antitubulin and anti-mitotic agents (U.S. Pat. Nos. 5,886,025; 6,162,930; 6,350,777; and 6,593,374; PCT publication no. WO 01/19794; Mullica et al., *J. Chem. Cryst.*, 1998; Pinney, et al., *Bioorg. Med. Chem. Lett.*, 1999). The lead compounds in each series demonstrate remarkable biological activity against a variety of human cancer cell lines.

In further support of our hypothesis, recent studies have shown that certain estrogen receptor (ER) binding compounds (ex. 2-methoxyestradiol) can interact with tubulin and inhibit tubulin assembly as structurally modified estradiol congeners (D'Amato et al., *Proc. Natl. Acad Sci,*. 1994; Cushman et al., *J. Med. Chem.*, 1995; Hamel et al., *Biochemistry*, 1996; Cushman et al., *J. Med. Chem.*, 1997). Estradiol is perhaps the most important estrogen in humans, and it is intriguing and instructive that the addition of the methoxy aryl motif to this compound makes it interactive with tubulin. It is also noteworthy that 2-methoxyestradiol is a natural mammalian metabolite of estradiol and may play a cell growth regulatory role especially prominent during pregnancy.

We undertook the design and synthesis of anti-mitotic agents based on a flavanoid molecular framework which designed to bind to the colchicine-binding site on β-tubulin. The synthesis of these compounds was initiated by the serendipitous synthesis of 3-aroylchromene derivatives and demonstration that these compounds have very good anti-mitotic activities with no appreciable side effects. Their flavanoid molecular framework was modified by the introduction of trimethoxyphenyl rings reminiscent of combretastatin A-4 and colchicine. These modified ligands were found to have no binding affinities towards ER but strong binding for tubulin. Our previous analysis of the structure-activity relationships of benzo[b]thiophene constructs have emphasized the importance of judicious placement of the trimethoxyphenyl ring and 4-methoxyphenyl rings. Pseudo π stacking of the two-aryl rings along with $sp^2$ hybridization at the bridge atoms between the rings is important for retaining tubulin binding properties. In addition to these factors, the centroid-to-centroid distances between the two-aryl rings are important. Optimization of this distance to approach that of CA-4 (4.7 Å) helps develop better ligands binding at the colchicine-binding site. A spacer ligand of two contiguous atoms had more freedom to align itself for a pseudo π stacking than the 1 atom-spacer ligand, and hence had better anti-mitotic activity. Similarly, restriction to free rotation by the introduction of a double bond resulted in better biological activity. Switching the positions of trimethoxyphenyl and 4-methoxyphenyl rings resulted in the reduction of anti-mitotic activity.

Surprisingly, the novel chromene-based ligands described herein, which are structurally related to CA4, have improved antiproliferative and vascular targeting activity over previously designed compounds. Clearly the ability to selectively disrupt the blood-flow to developing tumor cells is a potential breakthrough in the ever uphill battle against cancer. Certain flavanoids such as the 4-arylcoumarins (Bailly et al., *J. Med. Chem.*, 1998) have been shown to bind tubulin with high affinity, but they do not display antivascular properties. Additionally, unlike flavanoid compounds known in the art, the novel chromene compounds described in this application to be arranged in an appropriate molecular conformation such that a pseudo aryl-aryl pi stacking interaction can take place. Such an aryl-aryl interaction of the appropriate centroid-to-centroid distance (approximately 4.7 Angstroms) is believed to be important for enhanced binding affinity to the colchicine site on β-tubulin. It is this binding that ultimately leads to an inhibition of tubulin assembly which manifests itself as a cytotoxic event or antivascular event.

The 3-aroylchromene compounds in the present invention can be synthesized according to the following general scheme:

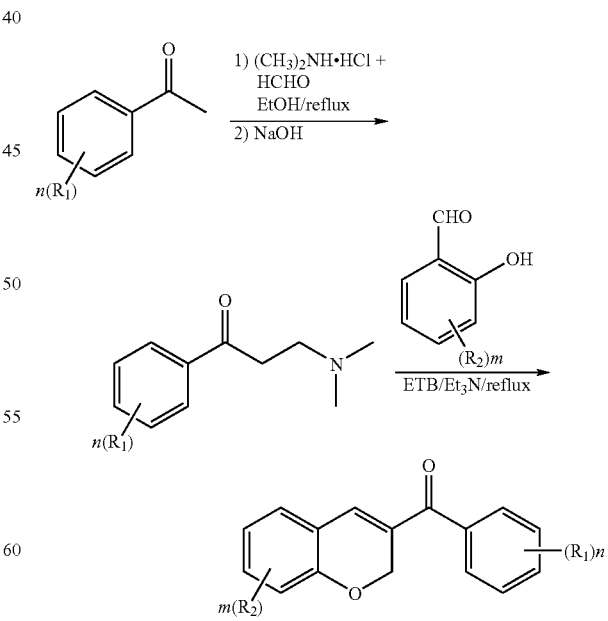

Subsequent treatment of the product of this reaction can be used to make the following derivatives using methods that are well known in the art:

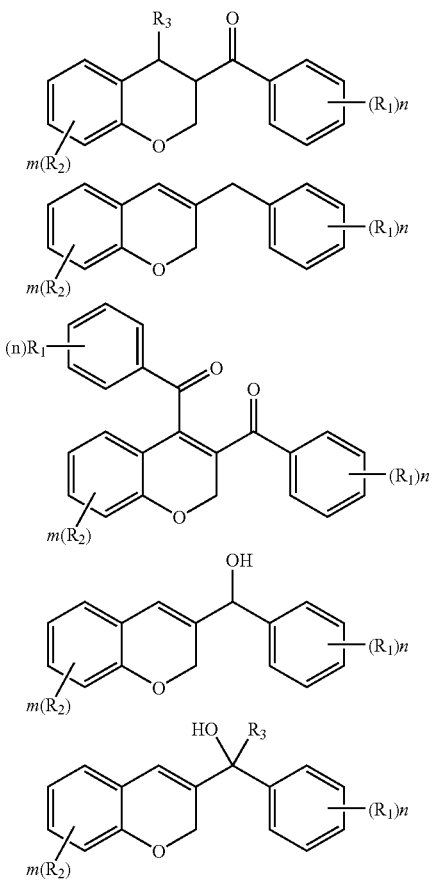

Treatment of Cancer and Other Malignant Proliferative Disorders

The chromene compounds of the present invention demonstrate remarkable cytotoxicity against a variety of human cancer cell lines. The ability of an agent to inhibit tubulin assembly and microtubule formation is an important property of many anticancer agents. Disruption of microtubules that comprise the cyto skeleton and mitotic spindle apparatus can interfere dramatically with the ability of a cell to successfully complete cell division. The compounds of the present invention are highly cytotoxic to actively proliferating cells, inhibiting their mitotic division and often causing their selective apoptosis while leaving normal quiescent cells relatively unaffected. Accordingly, the antiproliferative or anti-mitotic properties of the compounds of the present invention can be used to directly inhibit the proliferation of, or impart direct cytotoxicity towards, the cells of malignant or neoplastic tumors or cancers including:

1) carcinomas, such as those of the bladder, breast, colon, rectum, kidney, liver, lung (including small cell lung cancer), pharynx, esophagus, gall bladder, urinary tract, ovaries, cervix, uterus, pancreas, stomach, endocrine glands (including thyroid, adrenal, and pituitary), prostate, testicles and skin, including squamous cell carcinoma;
2) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;
3) hematopoietic tumors of myeloid lineage, including acute and chronic myelogenous leukemias, myelodysplastic syndrome and promyelocytic leukemia;
4) tumors of mesenchymal origin, including fibrosarcoma and rhabdomyosarcoma;
5) tumors of the central and peripheral nervous system and meninges, including astrocytoma, neuroblastoma, glioma, schwannomas, retinoblastomas, neuroma, glioma, glioblastoma; and
6) other tumors, including melanoma, seminoma, teratocarcinoma, osteosarcoma, xenoderoma pigmentosum, keratoctanthoma, thyroid follicular cancer, anaplastic thyroid cancer and Kaposi's sarcoma.

Alternatively, the compounds of the present invention can impart indirect control of the growth and proliferation of the above tumors and cancers due to their effects on malignant proliferating vasculature, such as the endothelium, arteries, blood vessels, or neovasculature formed by a tumor. These antivascular properties include, but are not limited to, the selective destruction, damage, or occlusion, whether reversible or irreversible, partial or complete, of proliferating tumor vasculature.

The compounds of the present invention may also be useful for the treatment of the tumors and cancer described above when used either alone or in combination with radiotherapy and/or other chemotherapeutic treatments conventionally administered to patients for treating solid tumor cancers. For example, compounds of the present invention may be administered with chemotherapeutic agents selected from one of the following mechanistic classes:

1. Alkylating agents: compounds that donate an alkyl group to nucleotides. Alkylated DNA is unable to replicate itself and cell proliferation is stopped. Exemplary alkylating agents include Melphalan, Chlorambucil, cyclophosphamide, ifosfamide, busulfan, dacarbaine, methotrexate, 5-FU, cytosine arabinsoide, or 6-thioguanine.
2. Antiangiogeneic agents: compounds that inhibit the formation of tumor vasculature. Exemplary anti-angiogenic agents include TNP-470 or Avastin™.
3. Antitumor Antibiotics: compounds having antimicrobial and cytotoxic activity. Such compounds also may interfere with DNA by chemically inhibiting enzymes and mitosis or altering cellular membranes. Exemplary anti-tumor antibiotics include Actinomycin-D, bleomycin, mitomycin-C, Dactinomycin, Daunorubicin, and Doxorubicin.
4. Topoisomerase Inhibitors: agents which interfere with topoisomerase activity thereby inhibiting DNA replication. Such agents include CPT-11 and Topotecan.
5. Hormonal Therapy: includes, but is not limited to antiestrogens. An exemplary antiestrogen is Tamoxifen.
6. Antimicrotubule compounds. Vincristine, paclitaxel, taxotere, etoposide, vinblastine, etc.

Treatment of Nonmalignant Vascular Proliferative Disorders

The invention provides the discovery that the compounds of the invention as well as analogs thereof, are vascular targeting agents (VTAs), and thus are also useful for the treatment of non-malignant vascular proliferative disorders, where the endothelium, artery, blood vessel, or neovasculature is not associated with a tumor but is nonetheless formed by undesirable or pathological angiogenesis. Such disease states include, without limitation:

1) ocular diseases such as wet or age-related macular degeneration, myopic macular degeneration, diabetic retinopathy, retinopathy of prematurity, diabetic molecular edema, uveitis, neovascular glaucoma, rubeosis, retrolental fibroplasias, angioid streaks, ocular histoplasmosis, and corneal neovascularization;
2) inflammatory disorders such as endometriosis, psoriasis, rheumatoid arthritis, Osler-Webber Syndrome, wound granulation, and
3) cardiovascular diseases such as atherosclerosis, atheroma, restenosis, haemangioma, restenosis.

In one preferred embodiment, the present invention is directed to the administration of compound of the invention for the treatment of non-malignant vascular proliferative disorders in the retinal tissue of the eye. Neovascularization of retinal tissue or "retinopathy" is a pathogenic condition characterized by vascular proliferation and occurs in a variety of ocular diseases with varying degrees of vision failure. The blood-retinal barrier (BRB) is composed of specialized non-fenestrated tightly-joined endothelial cells that form a transport barrier for certain substances between the retinal capillaries and the retinal tissue. The nascent vessels of the retina associated with the retinopathies are aberrant, much like the vessels associated with solid tumors. Tubulin binding agents, inhibitors of tubulin assembly, and vascular targeting agents may be able to attack the aberrant vessels because these vessels do not share architectural similarities with the BRB. Tubulin binding agents may halt the progression of the disease much like they do with a tumor-vasculature. The administration of a VTA for the pharmacological control of the retinal neovascularization associated with retinopathies as wet macular degeneration, proliferative diabetic retinopathy or retinopathy of prematurity, would potentially benefit patients for which few therapeutic options are available.

The compounds of the present invention are also contemplated for use in the treatment of vascular disease, particularly atherosclerosis and restenosis. Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells (VSMC) in the artery wall, which ordinarily control vascular tone, regulate blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much-accelerated form of the same pathogenic process that results in spontaneous atherosclerosis. Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop restenosis within 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30-50% of patients. Repeated revascularization surgery consumes time and money, is inconvenient to the patient, and can carry a significant risk of complications or death. The most effective way to prevent restenosis is at the cellular level.

Definitions

As used herein, the following terms in quotations shall have the indicated meanings, whether in plural or singular form:

"Amino acid acyl group" in the amino acid acylamino group is an acyl group derived from the amino acid. The amino acids may be enumerated by α-amino acids, βamino acids and γ-amino acids. Examples of preferred amino acids include glycine, alanine, leucine, serine, lysine, glutamic acid, aspartic acid, threonine, valine, isoleucine, ornithine, glutamine, asparagines, tyrosine, phenylalanine, cysteine, methionine, arginine, β-alanine, tryptophan, proline, histidine, etc. The preferred amino acid is serine and the preferred amino acid acyl group is a serinamide.

"Amine" refers to a free amine $NH_2$ or a lower alkylamino.

"Animal" refers to any warm-blooded mammal, preferably a human.

"Alkyl" refers to a group containing from 1 to 8 carbon atoms and may be straight chained or branched. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

"Aryl" refers to groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. The aromatic ring can be substituted at one or more ring positions with such substituents as described above, as for example, halogen, hydroxyl, alkoxy, etc. The preferred aryl group of the present invention is an optionally-substituted benzene ring of the following structure

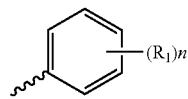

where $R_1$ is OH, Amine, or methoxy and n is 1, 2, or 3.

"Aroyl" refers to the —(C═O)-aryl groups, wherein aryl is defined as hereinabove. The aryl group is bonded to the core compound through a carbonyl bridge.

"Cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

"Flavanoids" are compounds having a core structure consisting of a 6-membered benzene ring conjugated to a 6-membered, heterocyclic ring in which the heteroatom is an oxygen. Compounds included within this group are chromenes, coumarins, flavanones, and flavones of the following structures:

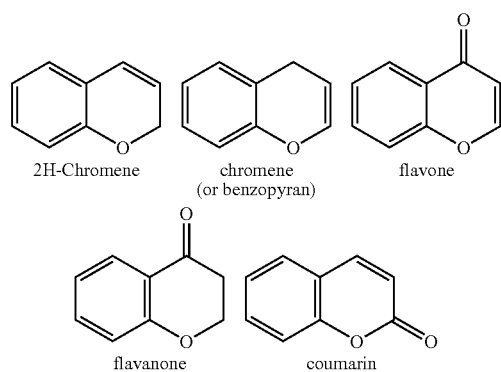

"Halogen" or "Halo" refers to chlorine, bromine, fluorine or iodine.

"Lower alkoxy" refers to —O-alkyl groups, wherein alkyl is as defined hereinabove. The alkoxy group is bonded to the core compound through the oxygen bridge. The alkoxy group may be straight-chained or branched; although the straight-chain is preferred. Examples include methoxy, ethyloxy, propoxy, butyloxy, t-butyloxy, i-propoxy, and the like. Preferred alkoxy groups contain 1-4 carbon atoms, especially preferred alkoxy groups contain 1-3 carbon atoms. The most preferred alkoxy group is methoxy.

"Lower alkylamino" refers to a group wherein one or two alkyl groups is bonded to an amino nitrogen, i.e., NH(alkyl). The nitrogen is the bridge connecting the alkyl group to the core compound. Examples include NHMe, NHEt, NHPr, and the like.

"Prodrug" refers to a precursor form of the drug which is metabolically converted in vivo to produce the active drug. Preferred prodrugs of the present invention include the phosphate, phosphoramidate, or amino acid acyl groups as defined herein. The phosphate ester salt moiety may also include (—OP(O)(O-alkyl)$_2$ or (—OP(O)(O—NH$_4^+$)$_2$).

"Phenolic moiety" means herein a hydroxy group when it refers to an R group on an aryl ring.

"Phosphate", "Phosphate moiety", or "Phosphate prodrug salt" refers to phosphate ester salt moiety (—OP(O)(O$^-$M$^+$)$_2$), a phosphate triester moiety (—OP(O)(OR)$_2$) or a phosphate diester moiety (—OP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Phosphoramidate" refers to a phosphoamidate ester salt moiety (—NP(O)(O$^-$M$^+$)$_2$), a phosphoramidate diester moiety (—NP(O)(OR)$_2$), or a phosphamidate disalts moiety (—NP(O)(OR)(O$^-$M$^+$), where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect.

"Salt" is a pharmaceutically acceptable salt and can include acid addition salts such as the hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li; alkali earth metal salts such as Mg or Ca; or organic amine salts such as those disclosed in PCT International Application Nos. WO02/22626 or WO00/48606.

"Treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

"Tubulin Binding Agent" shall refer to a ligand of tubulin or a compound capable of binding to either αβ-tubulin heterodimers or microtubules and interfering with the assembly or disassembly of microtubules.

"Effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

Dosage and Administration of Compounds

A typical daily dose will contain from about 0.1 mg/kg to about 1000 mg/kg of the active compound of this invention. Preferably, daily doses will be about 10 mg/kg to about 100 mg/kg, and most preferably about 10 mg.

In effecting treatment of a patient afflicted with a condition, disease or disorder described herein, a compound of the present invention can be administered systemically in any form or mode which makes the compound bioavailable in effective amounts. Systemic administration may be accomplished by administration of a compound of the present invention into the bloodstream at a site which is separated by a measurable distance from the diseased or affected organ or tissue. For example, compounds of the present invention can be administered orally, parenterally, subcutaneously, intramuscularly, intravenously, transdermally, intranasally, rectally, buccally, and the like. Oral or intravenous administration is generally preferred for treating neoplastic disease or cancer. Alternatively, the compound may be administered non-systemically by local administration of the compound of the present invention directly at the diseased or affected organ or tissue. Treatment of ocular diseases characterized by the presence of non-malignant proliferative vasculature or neovascularization, can be achieved using non-systemic administration methods such as intravitreal injection, sub-Tenon's injection, ophthalmic drops, iontophoresis, topical formulation and implants and/or inserts. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

According to another aspect, the present invention provides a pharmaceutical composition, which comprises a compound of the present invention or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well know in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

Alternatively, compounds of the present invention can be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The compositions in liposome form can contain, in addition to a compound of the present invention, stabilizers, preservatives, excipients, and the like. The preferred lipids are the phospholipids and the phosphatidylcholines (lecithins), both natural and synthetic. Methods to form liposomes are well known in the art (see for example, Prescott Ed., Methods in Cell Biology, Volume XIV, Academic Press, New York, N.Y., 1976, p 33).

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose of calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Tablets or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can of course, be individual instances where higher or lower dosage ranges are merited, and such are within the scope of this invention.

The compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers an preservatives as may be required.

"Administering" means any of the standard methods of administering a compound to a subject, known to those skilled in the art. Examples include, but are not limited to intravenous, intramuscular or intraperitoneal administration.

For the purposes of this invention "pharmaceutically acceptable carriers" means any of the standard pharmaceutical carriers. Examples of suitable carriers are well known in the art and may include, but are not limited to, any of the standard pharmaceutical carriers such as a phosphate buffered saline solutions, phosphate buffered saline containing POLYSORB 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay gelatin, stearic acid or salts thereof, magnesium or calcium stearate, talc, vegetable fats or oils, gums glycols, or other known excipients. Such carriers may also include flavor and color additives or other ingredients. Compositions comprising such carriers are formulated by well known convention methods.

Methods of determining an "effective amount" are well known to those skilled in the art and depend upon factors including, but not limited to, the size of the patient and the carrier used.

EXAMPLES

The invention is further defined by reference to the following examples and preparations which describe the manner and process of making and using the invention and are illustrative rather than limiting. It will be apparent to those skilled in the art that many modifications, both to the materials and methods, may be practiced without departing from the purpose and interest of the invention.

Materials and Methods

Chemicals were commercially obtained from the Aldrich Chemical Company, Fisher Scientific and ACROS Chemicals and used directly as purchased. Solvents such as acetone, diethylether and ethylacetate were used as purchased, and other solvents were purified by standard procedures. Tetrahydrofuran (THF) was dried over potassium metal and benzophenone and distilled freshly prior to use; methylene chloride ($CH_2Cl_2$) was dried using calcium hydride and distilled prior to use. Triethyl amine was distilled over calcium hydride and stored in a sealed bottle.

Reactions were followed by thin layer chromatography (TLC) and/or gas chromatography. Purification of products was carried out using flash column chromatography with silica gel. Silica gel plates for thin layer chromatography and silica gel (260-400 mesh) for column chromatography were obtained from Merck EM Science.

$^1$H and $^{13}$C NMR spectra were recorded in deuterated chloroform or deuterated methyl sulfoxide or deuterium oxide using an AMX 360 MHz (90 MHz for $^{13}$C, and 145 MHz for $^{31}$P) or a DPX Avance 300 MHz (75 MHz for $^{13}$C, and 120 MHz for $^{31}$P) Brüker NMR spectrometer. Peaks are listed as singlet (s), doublet (d), doublet of doublet (dd), triplet (t), or multiplet (m) with the coupling constant (j) expressed in Hz. High-resolution mass spectra were obtained using a VG/Fisons GC/NASS High Resolution Mass Spectrometer. Elemental analyses were obtained from Atlantic Microlab Inc., Norcross, Ga. Melting points were determined using a Thomas-Hoover melting point apparatus and are uncorrected.

Example 1

Synthesis of 3-Aroylchromene Analogs and Corresponding Prodrugs

The exemplary chromene (3',4',5'-Trimethoxybenzoyl)-7-methoxy-8-(t-butyldimethylsilyloxy)-2H-chromene and its corresponding phosphate prodrug was synthesized as described in FIG. 1. Under Stetter conditions, the free base amine 4 and diol 2 condensed into the expected phenol 5 in reasonable yield.

X-ray crystallography confirmed the structure of 5 to be a unique chromene derivative, which had the trimethoxybenzoyl group in the β position with respect to the aryl ring.

i) 2,3-Dihydroxy-4-methoxy-benzaldehyde, 2

2,3,4-trimethoxybenzaldehyde, 1 (9.8 g, 50 mmol) was dissolved in anhydrous dichloromethane (150 ml) under argon at ambient temperature. It was stirred for 10 minutes and boron trichloride (100 ml, 100 mmol, 2 eq; 1.0M solution in dichloromethane) was added. The dark reaction mixture was stirred for 24 hours and then slowly poured into 10% sodium bicarbonate (aq) (40 g/360 ml). The resulting solution was acidified with concentrated hydrochloric acid to pH 1. The dichloromethane layer was separated and the aqueous layer was extracted with ethyl acetate (4×100 ml) and dried. Evaporation of the solvent in vacuo gave a brown oil which was absorbed onto silica gel and subjected to flash chromatography (70:30, hexane-ethyl acetate). The diol 2 was obtained as a pale yellow solid (6.70 g, 80%).

$^1$H-NMR (300 MHz, CDCl$_3$) δ 3.99(3H, s, OCH$_3$), 5.54 (1H, s, OH), 6.62(1H ArH), 7.14(1H, d, J=8.04 Hz, ArH), 9.75(1H, s, CHO), 11.12(1H, s, OH); $^{13}$C-NMR (75 MHz, CDCl$_3$) δ 195.21, 153.05, 149.08, 133.05, 126.10, 116.11, 103.66, 56.39.

ii) 3-Dimethylamino-1-(3,4,5-trimethoxy-phenyl)-propan-1-one, 4

A mixture of 3',4',5'-Trimethoxyacetophenone 3(42.20 g, 200 mmol), dimethylamine hydrochloride (16.31 g, 200 mmol), paraformaldehyde (9 g, 300 mmol), concentrated hydrochloric acid (1.5 ml), and ethanol (80 ml) under argon was refluxed for 1.5 hours. Then one equivalent of paraformaldehyde (6 g, 200 mmol) was added to it and it was heated under reflux for another 6 hours. 300 ml acetone was added and the solution refluxed for about 15 minutes. A white solid was obtained which was crystallized in the refrigerator overnight, filtered and dried. The amine hydrochloride thus obtained was neutralized with 1M NaOH, extracted with ethyl acetate, washed with saturated sodium chloride, and dried over anhydrous magnesium sulfate. Evaporation of the solvent in vacuo gave the free base amine 4 as a yellowish brown oil (27.60 g, 52%).

$^1$ H-NMR (300 MHz, CDCl$_3$) δ 2.31 (6H, s, 2×CH$_3$), 2.76 (2H, t, CH$_2$), 3.14(2H, t, CH$_2$), 3.92(9H, s, 3×OCH$_3$), 7.24 (2H, s, J=3.54 Hz, ArH). $^{13}$C-NMR (75 MHz, CDCl$_3$) δ 196.59, 152.09, 141.60, 131.25, 104.64, 59.18, 55.14, 53.69, 44.50, 35.68.

iii) 3-(3',4',5'-Trimethoxybenzoyl)-7-methoxy-8-hydroxy-2H-chromene, 5

A mixture of 2-(N,N-dimethylamino)ethyl-(3',4',5'-trimethoxyphenyl)ketone (4, 1.17 g, 4.37 mmol), 2,3-dihydroxy-4-methoxybenzaldehyde (2, 0.74 g, 4.37 mmol), 3-ethyl-5-(2-hydroxyethyl)-4-methylthiazolium bromide (0.12 g, 0.44 mmol) and Et$_3$N (1 ml) was heated under reflux at 115° C. for 3.5 hours. After quenching with 1M HCl, the product was extracted with CH$_2$Cl$_2$. The combined extract was washed with water, rinsed with brine and dried over anhydrous magnesium sulfate. Purification was done by silica gel flash column chromatography (60:40, hexane-ethyl acetate) which afforded the pure yellow-colored phenol (0.179 g, 0.48 mmol) in 11% yield. The phenol had a melting point of 189-190° C.

$^1$ H NMR (300 MHz, CDCl$_3$) δ 3.91(6H, s, 2×OCH$_3$), 3.94(6H, s, 2×OCH CH$_2$), 5.50(1H, s, OH), 6.54(1H, d, J=8.5 Hz, ArH), 6.71 (1H, d, J=8.5 Hz, 1H), 6.97(2H, s, ArH), 7.17(1H, s, CH=C). $^{13}$C-NMR (75 MHz, CDCl$_3$) δ 193.58, 153.43, 150.85, 142.80, 141.85, 137.47, 134.09, 133.30, 128.27, 121.02, 115.81, 106.88, 105.10, 6.28, 61.40, 56.77, 56.70.

Anal. Calcd for C$_{20}$H$_{20}$O$_7$: C, 64.51; H, 5.41; O, 30.08. Found C, 64.48; H, 5.41; O, 30.25.

iv) Dibenzyl phosphate, 6

To a stirred solution of the phenol (0.2 g, 0.54 mmol) in acetonitrile (1 ml) under Argon cooled to −20° C. was added carbon tetrachloride (0.26 ml, 2.70 mmol). The resulting solution was stirred for 10 minutes prior to adding diisopropylethylamine (0.21 ml, 1.13 mmol) and DMAP (0.01 g, 0.11 mmol). Approximately 1 minute later, the slow dropwise addition of dibenzyl phosphate was done maintaining the temperature below −20° C. After 45 minutes, 0.5M KH$_2$PO$_4$ was added and the mixture was allowed to warm to room temperature. An ethyl acetate extract was washed with saturated sodium chloride (aq), followed by water and dried. Removal of the solvent in vacuo gave a yellow oil that was further separated by silica gel chromatography (flash, 60:40, hexane-ethyl acetate) to afford (0.34 g, 0.54 mmol, 100%) of the dibenzylphosphate as a clear green oil.

$^1$H-NMR (300 MHz, CDCl$_3$) δ 3.78(3H, s, OCH$_3$), 3.89 (6H, s, 2×OCH$_3$), 3.92(3H, s, OCH$_3$), 5.11(2H, s, CH$_2$), 5.31(4H, m, 2×CH$_2$-Ph), 6.54(1H, d, J=8.59 Hz), 6.94(1H, d, J=8.66 Hz, ArH), 6.97(2H, s, ArH), 7.15(1H, s, ArH), 7.37 (10H, m, 2×C$_6$H$_5$); $^{13}$C-NMR (75 MHz, CDCl$_3$) δ 192.60, 154.63, 154.59, 152.79, 147.63, 147.58, 141.31, 136.11, 135.78, 135.68, 132.47, 128.41, 128.27, 128.15, 127.89, 127.48, 125.88, 115.44, 106.25, 104.98, 69.52, 69.44, 65.51, 60.67, 60.09, 56.09, 55.94; $^{31}$ P-NMR (120 MHz, CDCl$_3$) 67 −5.56 v) 3-(3',4',5'-Trimethoxybenzoyl)-7-methoxy-2H-chromene-phosphate salt, 7

The dibenzylphosphate (0.19 g, 0.30 mmol) was dissolved in acetonitrile (11.0 ml), under Argon, cooled to 0° C. and bromotrimethylsilane (0.12 ml, 0.902 mmol) was added to it. After about 3 hours, TLC confirmed completion of the debenzylation, the reaction mixture was then treated with sodium methoxide (25 wt % in methanol, 0.21 ml, 0.902 mmol) and allowed to stir overnight. The product was filtered and dried to give 74% (0.11 g, 0.221 mmol) of the pure salt.

$^1$H-NMR (300 MHz, D$_2$O) δ 3.72(3H, s, OCH$_3$), 3.74(6H, s, 2×OCH$_3$), 3.77(3H, s OCH$_3$), 4.92(2H, s, CH$_2$), 6.56(1H, d, J=8.62 Hz, ArH), 6.80(1H, d, J=8.66 Hz, ArH), 6.84(2H, s, ArH), 7.03(1H, s, CH=C) $^{31}$P-NMR (120 MHz, D$_2$O) δ−3.01

The following chromenes were made in a manner similar to the synthetic route depicted in FIG. 1.

vi) 3-(3',4',5'-Trimethoxybenzoyl)-7-methoxy-2H-chromene (8, 0.108 g, 0.30 mmol, 15% yield): $^1$H-NMR (300 MHz, CDCl$_3$) δ $^1$H-NMR (300 MHz, CDCl$_3$) δ 3.82 (3H, s, OCH$_3$), 3.90(6H, s, 2×OCH$_3$), 3.93(3H, s, OCH$_3$), 5.13(2H, bs, CH$_2$), 6.47(1H, d, J=2.4 Hz, ARH), 6.52(1H, dd, J=8.4 Hz, 2.4 Hz, ArH), 6.96(1H, s, ArH), 7.05(1H, d, J=8.4 Hz, ArH), 7.17(1H, s, 1H, CH=C); $^{13}$C-NMR (75 MHz, CDCl$_3$) δ 193.03, 163.51, 157.23, 152.94, 137.17, 133.00, 130.47, 126.68, 114.18, 108.64, 106.30, 101.51, 65.57, 60.94, 60.38, 56.28, 55.51, 14.16.

Anal calcd. for C$_{20}$H$_{20}$O$_6$: C, 67.41; H, 5.66; O, 26.94. Found C, 67.20; H, 5.63; O, 27.09

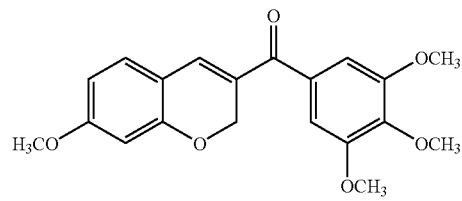

vii) 3-(3',4',5'-Trimethoxybenzoyl)-6-hydroxy-7-methoxy-2H-chromene (9, 0.30 g, 0.81 mmol, 12.16% yield): $^1$H-NMR (300 MHz, CDCl$_3$) δ 3.90(6H, s, 2×OCH$_3$), 3.92(3H, s, OCH$_3$), 3.93(3H, s, OCH$_3$), 5.08((2H, s, CH$_2$), 6.50(1H, s, ArH), 6.69(1H, s, ArH), 6.96(2H, s, ArH), 7.11(1H, s, CH=C); $^{13}$C-NMR (75 MHz, CDCl$_3$) δ 192.95, 153.70, 150.30, 149.96, 141.57, 140.61, 137.09, 133.00, 127.48, 113.82, 113.66, 106.59, 99.72, 65.56, 60.99, 56.38, 56.21.

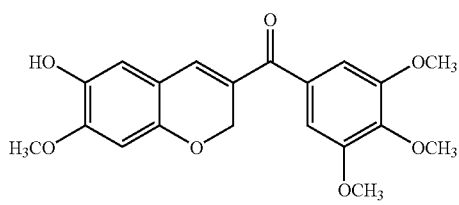

viii) 3-(3',4',5'-Trimethoxybenzoyl)-6-phosphate-7-methoxy-2H-chromene disodium salt (10, 0.04 g, 0.08 mmol, 58% yield): $^1$H-NMR (300 MHz, D$_2$O) δ 3.76(6H, s, 2×OCH$_3$), 3.83(6H, s, 2×OCH$_3$), 4.90 (2H, s, CH$_2$), 6.52(1H, s, ArH), 6.89(2H, s, ArH), 7.06(1H, s ArH), 7.13(1H, s, CH=C); $^{31}$P-NMR (120 MHz, D$_2$O) δ−2.77.

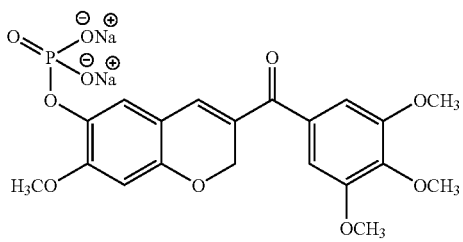

ix) 3-(3',4',5'-Trimethoxybenzoyl)-7-methoxy-8-fluoromethoxy-2H-chromene (11, 0.22 g, 0.55 mmol, 28% yield): $^1$ H-NMR (300 MHz, CDCl$_3$) δ 3.90(9H, s, 3×OCH$_3$), 3.94(3H, s, OCH$_3$), 5.15(2H, s, CH$_2$), 5.59(2H, d, OCH$_2$F, J=51.18 Hz), 6.57(1H, d, J=8.58 Hz, ArH), 6.95(1H, d, J=858 Hz), 6.98(2H, s, ArH), 7.15(1H, s, CH=C) $^{13}$ C-NMR (75 MHz, CDCl$_3$) δ 192.90, 155.80, 153.05, 148.77, 141.60, 136.41, 133.16, 132.74, 127.90, 126.00, 119.39, 115.80, 106.55, 105.31, 102.15, 65.86, 60.97, 56.38, 56.30 Structure confirmed by DEPT 45, 90, 135; $^{19}$ F-NMR (282 MHz, CDCl$_3$) 67 −146.09.

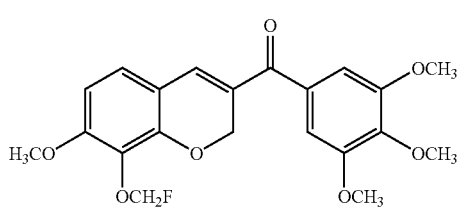

x) 3-(3',4',5'-Trimethoxybenzoyl)-7,8-dimethoxy-2H-chromene (12, 0.24 g, 0.62 mmol, 3% yield): $^1$ H-NMR (300 MHz, CDCl$_3$) δ 3.90(6H, s, 2×OCH$_3$), 3.91(3H, s, OCH$_3$), 3.93(3H, s, OCH$_3$), 5.18(2H, s, CH$_2$), 6.53(1H, d, J=8.52 Hz), 6.89(1H, d, J=8.49 Hz), 6.97(2H, s, ArH), 7.15(1H, s, CH=C); $^{13}$ C-NMR (75 MHz, CDCl$_3$) δ 193.00, 156.41, 153.08, 148.93, 141.59, 137.32, 136.91, 132.93, 127.70, 124.63, 115.88, 106.60, 105.35, 65.73, 61.12, 61.00, 56.42, 56.17.

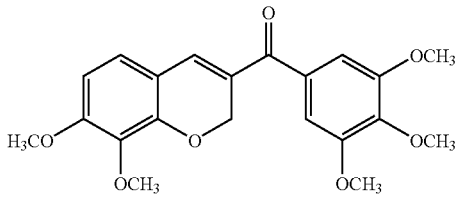

xi) 3-(3',4',5'-Trimethoxybenzoyl)-6,7-dimethoxy-2H-chromene (13, 0.11 g, 29 mmol, 3% yield): $^1$ H-NMR (300 MHz, CDCl$_3$) δ $^1$ H-NMR (300 MHz, CDCl$_3$) δ 3.83(3H, s, OCH$_3$), 3.91(6H, s, 2×3 OCH$_3$), 3.93(3H, s, OCH$_3$), 5.10(2H, s, CH$_2$), 6.52(1H, s, ArH), 6.57(1H, s, ArH), 6.96(2H, s, ArH), 7.15(1H, s, CH=C) $^{13}$C-NMR (75 MHz, CDCl$_3$) δ 192.92, 152.99, 151.14, 144.30, 141.34, 137.30, 133.12, 126.86, 112.81, 111.16, 107.17, 106.45, 105.63, 100.38, 65.54, 60.93, 56.38, 56.12

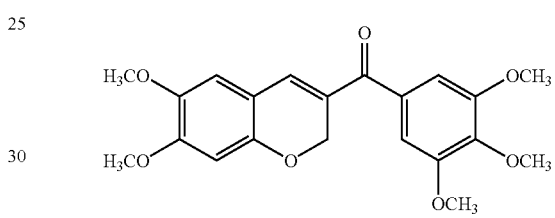

xii) 3-(3',4',5'-Trimethoxybenzoyl)-5,7-dimethoxy-2H-chromene (14, 0.12 g, 0.31 mmol, 1.5% yield): $^1$ H-NMR (300 MHz, CDCl$_3$) δ 3.79(3H, s, OCH$_3$), 3.81(3H, s, OCH$_3$), 3.90(6H, s, 2×OCH$_3$), 3.94(3H, s, OCH$_3$), 5.09(2H, s, CH$_2$), 6.04(1H, d, J=8.2.13 Hz, ArH), 6.12(1H, d, J=2.05 Hz, ArH), 7.00(2H, s, ArH), 7.52(1H, s, CH=C); $^{13}$ C-NMR (75 MHz, CDCl$_3$) δ 192.82, 164.46, 158.48, 158.02, 152.95, 141.25, 133.33, 132.93, 124.49, 106.64, 104.85, 93.54, 92.29, 65.34, 60.95, 56.32, 55.68, 55.59

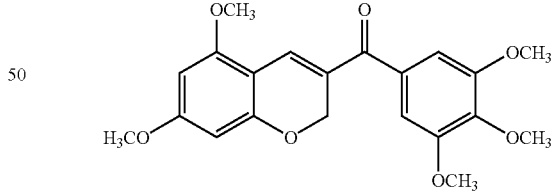

xiii) 3-(3',4',5'-Trimethoxybenzoyl)-8-hydroxy-2H-chromene (15, 1.94 g, 5.67 mmol, 15.7% yield): $^1$H-NMR (300 MHz, DMSO) δ 3.91(6H, s, 2×OCH$_3$), 3.94(3H, s, OCH$_3$), 5.19 (2H, d, CH$_2$), 5.63(1H, s, OH), 6.72(1H, dd, J=7.57 Hz, J=1.51 Hz, ArH), 6.86(1H, t, J=7.98 Hz, ArH), 6.97(1H, dd, J=8.07 Hz, J=1.54 Hz, ArH), 6.99(2H, s, ArH), 7.19(1H, s, —CH=C); $^{13}$ C-NMR (75 MHz, DMSO) δ 193.56, 153.49 144.88, 142.22, 136.80, 132.85, 130.33, 122.57, 121.58, 120.99, 118.96, 107.02, 66.35, 61.40, 56.79.

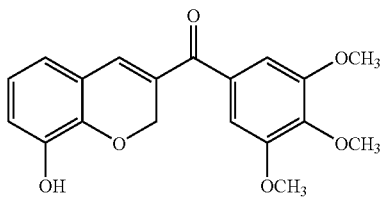

xiv) 3-(3',4',5'-Trimethoxybenzoyl)-8-phosphate-2H-chromene disodium salt (16, 0.20 g, 0.43 mmol, 50% yield): $^1$H-NMR (300 MHz, DMSO) δ 3.75(3H, s, OCH$_3$), 3.84(6H, s, 2×OCH$_3$), 5.02 (1H, s, CH$_2$), 6.85(1H, t, J=7.91 Hz, ArH), 7.02(2H, s, ArH), 7.10 (1H, d, J=6.94 Hz, ArH), 7.37(1H, s, —CH=C), 7.39 (1H, d, J=8.15 Hz, ArH); $^{13}$C-NMR (75 MHz, DMSO) δ 192.24, 152.59, 145.55, 145.46, 140.80, 136.16, 132.17, 129.33, 123.95, 123.82, 122.25, 120.95, 106.37, 64.59, 60.04, 55.96; $^{31}$P-NMR (120 MHz, DMSO) 67 −4.70

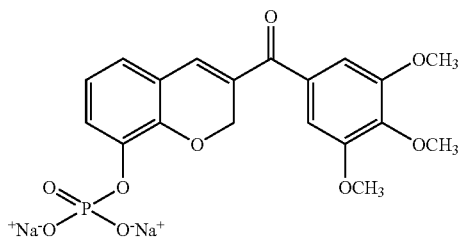

xv) 3-(3',4',5'-Trimethoxybenzoyl)-7,8-dihydroxy-2H-chromene (17, 0.1 g, 27.90 mmol 15.0% yield): $^1$H-NMR (300 MHz, DMSO) δ 3.78(3H, s, OCH$_3$), 3.82(6H, s, 2×OCH$_3$), 4.98 (1H, s, CH$_2$), 6.41(1H, d, J=8.10 Hz, ArH), 6.75(1H, d, J=8.31 Hz, ArH), 6.94(2H, s, ArH), 7.29(1H, s, —CH=C); $^{13}$C-NMR (75 MHz, DMSO) δ 192.02, 152.54, 150.39, 143.71, 140.39, 132.93, 132.81, 125.32, 121.00, 113.69, 109.37, 106.15, 64.55, 60.02, 55.94

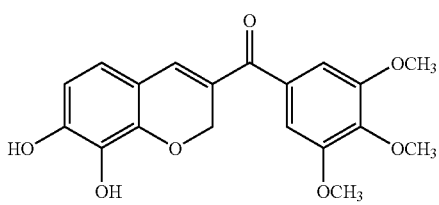

xvi) 3-(3',4',5'-Trimethoxybenzoyl)-7,8-diphosphate-2H-chromene tetrasodium salt (18, 0.07 g, 0.12 mmol, 44.4% yield): $^1$H-NMR (300 MHz, D$_2$O) δ 3.70(3H, s, OCH$_3$), 3.71(6H, s, 2×OCH$_3$), 4.96(2H, s, CH$_2$), 6.87(4H, s, ArH), 7.09(1H, s, —CH=C); $^{31}$P-NMR (120 MHz, D$_2$O) δ−2.99, −2.59,

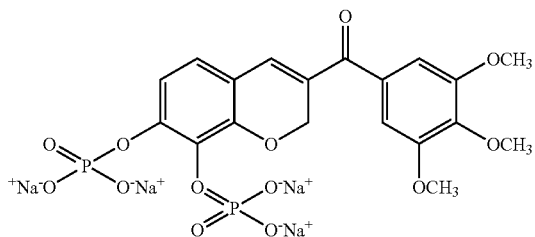

Example 2

Synthesis of Nitrogenated 3-Aroylchromene Analogs

In addition to the phosphate ester prodrugs that are described in this application for chromene-based anti-mitotic agents, it is envisioned that phosphorous based prodrug derivatives of nitrogenated chromenes may have therapeutic advantages as selective tumor vasculature destruction agents. These compounds are primarily serinamides, phosphoramidates, and related phosphate dianions that are assembled on an amino substituent of a chromene analog. When utilized in vivo, phosphoramidate analogs are able to provide a more soluble compound than the corresponding amine, thereby increasing the bioavailability of the parent drug. The P—N bond can be enzymatically cleaved by serum phosphatases releasing the amine which can inhibit tubulin assembly in a manner analogous to CA4P.

Furthermore, the carbonyl group of the benzoyl substituent can be replaced with an oxygen to generate a new compound which maintains the same or similar biological efficacy with tubulin. These compounds may be prepared by an addition elimination reaction utilizing the trimethoxyphenolic anion as a nucleophile. Other linkage atoms between the aryl-aryl rings are conceivable as well, including thioethers (—S—), secondary alcohols (—CH(OH)—, and methylenes (—CH$_2$—). These compounds are intended to form a one-atom bridge between the substituted aryl and the chromene ring. For example, the secondary alcohols can be created by reduction of corresponding ketones (—C=O)— with sodium borohydride, and methylenes can be created by reduction with trifluoroacetic acid. Alternatively, a single covalent bond can substitute for the 1-atom linker.

Example 3

Inhibition of Tubulin Polymerization

IC$_{50}$ values for tubulin polymerization were determined according to a previously described procedure (Bai et al., Cancer Research, 1996). Purified tubulin is obtained from bovine brain cells as previously described (Hamel and Lin, Biochemistry, 1984). Various amounts of inhibitor were pre-incubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM $MgCl_2$, 4% DMSO and 0.1M 4-morpholineethanesulfonate buffer (MES, pH 6.4). $IC_{50}$ is the amount of inhibitor needed to inhibit tubulin polymerization 50% with respect to the amount of inhibition that occurs in the absence of inhibitor.

TABLE 1

In Vitro Inhibition of Tubulin Polymerization.

| Compound | $IC_{50}$ (µM) |
|---|---|
| CA-4 | 0.73 |
| 5 | 1-2 |
| 8 | 4-10 |
| 9 | >40 |
| 10 | |
| 11 | |
| 12 | 20 |
| 13 | 20 |
| 14 | 20 |
| 15 | 2-4 |
| 16 | >40 |

TABLE 1-continued

In Vitro Inhibition of Tubulin Polymerization.

| Compound | $IC_{50}$ (µM) |
|---|---|
| 17 | 10-20 |
| 18 | >40 |

Example 4

In Vitro Cytotoxicity Activity Against Cancer Cell Lines

Newly prepared compounds were evaluated for cytotoxic activity against a variety of cell lines derived from human tumors using an assay system similar to the National Cancer Institute procedure previously described (Monks et al, J. Natl. Cancer Inst., 1991). Briefly, the cell suspensions, diluted according to the particular cell type and the expected target cell density (5,000-40,000 cells per well based on cell growth characteristics), were added by pipet (100 µl) to 96-well microtiter plates. Inoculates were allowed a preincubation time of 24-28 hours at 37° C. for stabilization. Incubation with the inhibitor compounds lasted for 48 hours in 50% $CO_2$ atmosphere and 100% humidity. Determination of cell growth was performed by in situ fixation of cells, followed by staining with a protein-binding dye sulforhodamine B (SRB), which binds to the basic amino acids of cellular macromolecules. The solubilized stain was measured spectrophotometrically.

Several compounds were evaluated for cytotoxic activity against human P388 leukemia cell lines. The effective dose or $ED_{50}$ value (defined as the effective dosage required to inhibit 50% of cell growth) was measured. These and additional compounds were evaluated in terms of growth inhibitory activity against several other human cancer cell lines including: central nervous system ("CNS", SF-268), pancreas (BXPC-3), non-small cell lung cancer ("lung-NCS", NCI-H460), breast (MCF-7), colon (KM20L2), ovarian (OVCAR-3), and prostate (DU-145). The results are described in Table 2 below. The growth inhibition $GI_{50}$ (defined as the dosage required to inhibit tumor cell growth by 50%) is listed for each cell line.

TABLE 2

In vitro Cytotoxicity against Human Cancer Cell Lines

| Compound | ED50 (µg/ml) for P-388 Cell Line | $GI_{50}$ (µg/ml) for Cell Line | | | | | |
|---|---|---|---|---|---|---|---|
| | | SF-268 | BXPC-3 | NCI-H460 | MCF-7 | KM20L2 | DU-145 |
| 5 | N.D. | 0.022 | 3.5 | 0.46 | 0.055 | 3.2 | 0.049 |
| 7 | 0.173 | 0.034 | 0.44 | 0.14 | 0.056 | 3.5 | 0.18 |
| 8 | 2.04 | 0.32 | 0.27 | 0.30 | 0.27 | 0.47 | 0.26 |
| 9 | 28.2 | >10 | 7.1 | 5.5 | 7.3 | >10 | 3.9 |
| 10 | N.D. | N.D. | N.D. | N.D. | N.D. | N.D. | N.D. |
| 11 | N.D. | N.D. | N.D. | N.D. | N.D. | N.D. | N.D. |
| 12 | 0.41 | 0.34 | 0.46 | 0.37 | 0.48 | 0.40 | 0.16 |
| 13 | 2.5 | 0.50 | 0.38 | 0.40 | 0.56 | 0.40 | 0.42 |
| 14 | 16.3 | 0.40 | 0.43 | 0.40 | 0.47 | 0.37 | 0.24 |
| 15 | 0.093 | 0.048 | 2.4 | 0.044 | 0.21 | 4.0 | 0.026 |
| 16 | 0.019 | 0.058 | 1.6 | 0.12 | 0.45 | 5.4 | 0.046 |
| 17 | 1.8 | 0.32 | 3.0 | 0.34 | 0.48 | 6.3 | 0.23 |
| 18 | 0.56 | 3.4 | >10 | 3.5 | 4.2 | >10 | 2.2 |

Example 5

Inhibition of Tumor Blood Flow

The antivascular effects of the chromene phosphate prodrug were assessed in tumor-bearing mice using a Fluorescent Bead Assay. A MHEC-5T hemangioendothelioma tumor model was established by subcutaneous injection of $0.5 \times 10^6$ cultured transformed cell murine myocardial vascular endothelial cell line ("MHEC5-T") cells into the right flank of Fox Chase CB-17 Severe Combined Immunodeficient ("SCID") mice. When transplanted tumors reached a size of 500 $mm^3$ (a size without development of necrosis), the mice received a single intraperitoneal (i.p.) injection of saline control or compound at doses ranging from 3.2 to 25 mg/kg. At 24 hours post-treatment, mice were injected intravenously with 0.25 ml of diluted FluoSphere beads (1:6 in physiological saline) in the tail vein, sacrificed after 3 minutes, and tumor was excised for cryosectioning. Tumor cryosections at a thickness of 8 um were directly examined using quantitative fluorescent microscopy. Blood vessels were indicated by blue fluorescence from injected beads. For quantification, image analysis of 3 sections from three tumors treated in each group were examined and vascular shutdown was expressed as vessel area (mm$^2$) per tumor tissue area (mm$^2$) as a percentage of the control ("% VAPM").

TABLE 3

Vascular Targeting Activity of Chromenes

| Compound | % VAPM at 100 mg/kg dose | % VAPM at 10 mg/kg dose |
|---|---|---|
| 5 | 90 | 80 |
| 7 | 33 | 57 |

Example 6

Evaluation of Tumor Growth Control In Vivo by Hollow Fiber Assay

Human tumor cells were grown in polyvinylidene fluoride (PVDF) hollow fibers and each cell line was injected into the mice intraperitoneal (IP) and subcutaneous (SC) membrane compartments. Mice were injected intraperitoneally with two different test doses of the potential anti-tumor agent. The control animals are injected with the diluent. Formazan dye (MTT) conversion assay was used to determine viable cell mass for the assessment of the anti-cancer effects of the ligand. The % T/C is calculated using average optical density of the compound treated sample divided by the average optical density of the control animals.

ALTERNATIVE EMBODIMENTS

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

It should be readily apparent to any practitioner skilled in the art that there are various ways of appending trimethoxyaryl and trimethoxyaroyl groups around a chromene molecular scaffold in a manner which will result in a similar molecular conformation capable of undergoing pseudo pi-pi stacking. In addition, although the trimethoxyaryl motif seems optimal for enhanced tubulin binding, it is also very possible that another combination of alkoxy substituents (such as ethoxy, propoxy, isopropoxy, allyloxy, etc.) either as a trisubstituted pattern or as disubstituted (with one type of alkoxy moiety) and monosubstituted (with a different alkoxy moiety), or with three distinct types of alkoxy moieties may also have good tubulin binding characteristics. It is also conceivable that instead of having aryl alkoxy groups, it may be possible to substitute simply aryl-alkyl and aryl-alkenyl moieties and still maintain the enhanced cytotoxicity profile.

Phenolic groups may also have activity on these described chromene ligands. The synthesis of any of these modified chromene-ligands will be very straight-forward for anyone skilled in the art, and often will only involve a different choice of initial starting materials. To prepare these alternative ligands, the same synthetic schemes as disclosed herein or similar schemes with only slight modifications may be employed.

REFERENCES

The following citations are incorporated in pertinent part by reference herein for the reasons cited.

(1) Bai, R.; Schwartz, R. E.; Kepler, J. A.; Pettit, G. R.; Hamel, E., Characterization of the Interaction of Cryptophycin with Tubulin: Binding in the Vinca Domain, Competitive Inhibition of Dolastatin 10 Binding, and an Unusual Aggregation Reaction, *Cancer Res.*, 1996, 56, 4398-4406.

(2) Bai, R.; Schwartz, R. E.; Kepler, J. A.; Pettit, G. R.; Hamel, E., Characterization of the Interaction of Cryptophycin with Tubulin: Binding in the Vinca Domain, Competitive Inhibition of Dolastatin 10 Binding, and an Unusual Aggregation Reaction, *Cancer Res.*, 1996, 56, 4398-4406.

(3) Bailly, C, Bal C, Barbier P, Combes S, Finet J-P, Hildebrand M-P, Peyrot V, Wattez N. Synthesis and biological evaluation of 4-Arylcoumarin analogues of Combretastatins. Journal of Medicinal Chemistry. 2003. 46, 5437-44.

(4) Boyd, M. R.; Paull, K. D., Some Practical Considerations and Applications of the National Cancer Institute In Vitro Anticancer Drug Discovery Screen, *Drug Development Research*, 1995, 34, 91.

(5) Chaplin, D. J.; Dougherty, G. J. Tumor vasculature as a target for cancer therapy. Br. *J. Cancer Therapy.* 1999, 80(Suppl. 1), 57-64.

(6) Chaplin D J, Pettit G R, Hill S A. Anti-vascular approaches to solid tumor therapy: Evaluation of combretastatin A4 phosphate. *Anticancer Res.,* 1999; 19:189-196.

(7) Chaplin J H, Flynn B L. A multi-component coupling approach to benzo[b]furans and chromenes. *Chem. Commun.* 2001, 1594-5.

(8) Chavan, A. J.; Richardson, S. K.; Kim, H.; Haley, B. E.; Watt, D. S., Forskolin Photoaffinity Probes for the Evaluation of Tubulin Binding Sites, *Bioconjugate Chem.* 1993, 4, 268.

(9) Cortese, F.; Bhattacharyya, B.; Wolff, J., Podophyllotoxin as a Probe for the Colchicine Binding Site of Tubulin, *J. Biol. Chem.,* 1977, 252, 1134.

(10) Cushman, M.; He, H.-M.; Katzenellenbogen, J. A.; Varma, R. K.; Hamel, E.; Lin, C. M.; Ram, S.; Sachdeva, Y. P., Synthesis of Analogs of 2-Methoxyestradiol with Enhanced Inhibitory Effects on Tubulin Polymerization and Cancer Cell Growth, *J. Med. Chem.,* 1997.

(11) Cushman, M.; He, H-M.; Katzenellenbogen, J. A.; Lin, C. M.; Hamel, E., Synthesis, Antitubulin and Antimitotic Activity, and Cytotoxicity of Analogs of 2-Methoxyestradiol, an Endogenous Mammalian Metabolite of Estradiol That Inhibits Tubulin Polymerization by Binding to the Colchicine Binding Site, *J. Med. Chem.,* 1995, 38, 2041.

(12) Cushman, M.; Nagarathnam, D.; Gopal, D.; Chakraborti, A. K.; Lin, C. M.; Hamel, E. Synthesis and Evaluation of Stilbene and Dihydrostilbene Derivatives as Potential Anticancer Agents That Inhibit Tubulin Polymerization, *J. Med. Chem.* 1991, 34, 2579.

(13) D'Amato, R. J.; Lin, C. M.; Flynn, E.; Folkman, J.; Hamel, E., 2Methoxyestradiol, an endogenous mamalian metabolite, inhibits tubulin polymerization by interacting at the colchicine site, *Proc. Natl. Acad. Sci.* 1994, 91, 3964.

(14) Dark, G. G., Hill, S. A., Prise, V. G., Tozer, G. M., Pettit, G. R., Chaplin, D. J., Combretastatin A-4, an Agent That Displays Potent and Selective Toxicity Toward Tumor Vasculature, *Cancer Res.,* 1997, 57, 1829-1834

(15) Davis P D, Dougherty G J, Blakey D C, Galbraith S M, Tozer G M, Holder A L, Naylor M A, Nolan J, Stratford M R, Chaplin D J, Hill S A. ZD6126: A Novel Vascular-targeting Agent that causes selective destruction of tumor vasculature. *Cancer Research.* 2002. 62(24): 7247-53.

(16) Dorr, R. T.; Dvorakova, K.; Snead, K.; Alberts, D. S.; Salmon, S. E.; Pettit, G. R., Antitumor Activity of Combretastatin A4 Phosphate, a Natural Product Tubulin Inhibitor, Invest. *New Drugs,* 1996, 14, 131.

(17) Fischer, B.; and Sheihet, L., *J. Org. Chem.* 1998, 63, 393-395.

(18) Gerwick, W. H.; Proteau, P. J.; Nagle, D. G.; Hamel, B.; Blokhin, A.; Slate, D. L., Structure of Curacin A, a Novel Antimitotic, Antiproliferative, and Brine Shrimp Toxic Natural Product from the Marine Cyanobacterium Lyngbya majuscula, *J. Org. Chem.* 1994, 59, 1243.

(19) Gianna Kakou, P.; Sackett, D.; Fojo, T.; Tubulin/Microtubes: Still a promising Target for New Chemotherapeutic Agents, *J. Natl Cancer Inst.,* 2000, 92, 182.

(20) Grese, T. A.; Cho, S.; Finley, D. R.; Godfrey, A. G.; Jones, C. D.; Lugar III, C. W.; Martin, M. J.; Matsumoto, K.; Pennington, L. D.; Winter, M. A.; Adrian, M. D.; Cole, H. W.; Magee, D. E.; Phillips, D. L.; Rowley, E. R.; Short, L.; Glasebrook, A. L.; Bryant, H. R., Structure-Activity Relationships of Selective Estrogen Receptor Modulators: Modifications to the 2-Arylbenzothiophene Core of Raloxifene, *J. Med. Chem.,* 1997, 40, 146.

(21) Hadimani, M. B.; Kessler, R. J.; Kautz, J. A.; Ghatak, A.; Shirali, A. R.; O'Dell, H.; Garner, C. M.; Pinney, K. G. 2-(3-tert-Butyldimethylsiloxy-4-methoxyphenyl)-6-methoxy-3-(3, 4, 5-trimethoxybenzoyl)indole. *Acta Cryst.* 2002, C58, o330-o332.

(22) Hahn, K. M.; Hastie, S. B.; Sundberg, R. J., Synthesis and Evaluation of 2-Diazo-3,3,3-trifluoropropanoyl Derivatives of Colchicine and Podophyllotoxin as Photoaffinity Labels: Reactivity, Photochemistry, and Tubulin Binding, *Photochem. Photobiol.* 1992, 55, 17.

(23) Hamel, E.; Lin, C. M.; Flynn, E.; D'Amato, R. J. D., Interactions of 2-Methoxyestradiol, and Endogenous Mammalian Metabolite, with Unpolymerized Tubulin and with Tubulin Polymers, *Biochemistry,* 1996, 35, 1304.

(24) Hamel, E.; Lin, C. M., Separation of Active Tubulin and Microtubule-Associated Proteins by Ultracentrifugation and Isolation of a Component Causing the Formation of Microtubule Bundles, *Biochemistry,* 1984, 23, 4173-4184.

(25) Hamel, E.; Lin, C. M. Interactions of combretastatin, a new plant-derived antimitotic agent, with tubulin. *Biochem. Pharmacol.* 1983, 32, 3864-3867.

(26) Inion, H.; De Vogelaer, H.; Descamps, M.; Bauthier, J.; Colot, M.; Richard, J; Charlier, R. Study of the chromene series. IV. 2-Alkyl or 2-aryl 3-(4-aminoalkoxybenzoyl)indoles as potential antianginal and antiinflammatory compounds. *Eur. J. Med. Chem.* 1977, 12, 483-487.

(27) Iyer, S.; Chaplin, D. J.; Rosenthal, D. S.; Boulares, A. H.; Li, L. Y.; and Smulson, M. E., *Cancer Res.* 1998, 58, 4510-4514.

(28) Jiang, J. B.; Hesson, D. P.; Dusak, B. A.; Dexter, D. L.; Kang, G. J.; Hamel, B., Synthesis and Biological Evaluation of 2-Styrylquinazolin-4(3H)-ones, a New Class of Antimitotic Anticancer Agents Which Inhibit Tubulin Polymerization, J. Med. Chem. 1990, 33, 1721.

(29) Jones, C. K.; Jevnikar, M. G.; Pike, A. J.; Peters, M. K.; Black, L. J.; Thompson, A. R.; Falcone, J. F.; Clemens, J. A., Antiestrogens. 2. Structure-Activity Studies in a Series of 3-Aroyl-2-arylbenzo[b]thiophene Derivatives Leading to [6-Hydroxy-2-(4-hydroxyphenyl) benzo[b]thiphene-3-yl][4-[2-(1-piperidinyl) ethoxy] phenylimethanone Hydrochloride (LY156758), a Remarkably Effective Estrogen Antagonist with Only Minimal Intrinsic Estrogenicity, J. Med. Chem. 1984, 27, 1057.

(30) Kanthou C, Tozer G M. The tumor vascular targeting agent CA4P induces reorganization of the actin cytoskeleton and early membrane blebbing in human endothelial cells. Blood. 2002. 99(6):2060-9.

(31) Lejeune P, Hodge T G, Vrignaud, Bissery M-C. In vivo antitumor activity and tumor necrosis induced by AVE8062A, a tumor vasculature targeting agent. Proceedings of the AACR. ABSTRACT#781. 2002, 43:156.

(32) Li Q and Sham H L. Discovery and development of antimitotic agents that inhibit tubulin polymerization for the treatment of cancer. Expert. Opin. Ther. Patents. 2002, 12(11): 1663-1702.

(33) Lin, C. M.; Ho, H. H.; Pettit, G. R.; Hamel, E., Antimitotic Natural Products Combretastatin A-4 and Combretastatin A-2: Studies on the Mechanism of Their Inhibition of the Binding of Colchicine to Tubulin, Biochemistry 1989, 28, 6984.

(34) Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich; Campbell; Mayo; Boyd, M., Feasibility of a High-Flux Anticancer Drug Screen Using a Diverse Panel of Cultured Human Tumor Cell Lines, J. Natl. Cancer Inst., 1991, 83, 757-766.

(35) Mossman, T. Rapid colorimetric assay for cellular growth and survival: application to proliferation and cytotoxicity assay. J. Immunol. Methods, 1983, 16, 195-200.

(36) Mullica, D. F.; Pinney, K. G.; Mocharla, V. P.; Dingeman, K. M.; Bounds, A. D.; Sappenfield, E. L., Characterization and Structural Analyses of Trimethoxy and Triethoxybenzo[b]thiophene, J. Chem. Cryst., 1998, 28, 289-295.

(37) Nicolaou, K. C., Winssinger, N., Pastor, J., Ninkovic, S., Sarabia, F., He, Y., Vourloumis, D., Yang, Z., Oi, T., Giannakakou, P., Hamel, B., Synthesis of Epothilones A and B in Solid and Solution Phase, Nature, 1997, 387, 268-272.

(38) Owellen, R. J.; Hartke, C. A.; Kickerson, R. M.; Hams, F. 0., Inhibition of Tubulin-Microtubule Polymerization by Drugs of the Vinca Alkaloid Class, Cancer Res. 1976, 36, 1499.

(39) Palkowitz, A. D.; Glasebrook, A. L.; Thrasher, K. J.; Hauser, K. L.; Short, L. L.; Phillips, D. L.; Muehl, B. S.; Sato, M.; Shetler, P. K.; Cullinan, G. J.; Pell, T. R.; Bryant, H. U., Discovery and Synthesis of [6-Hydroxy-3-[4-[2-(1-piperidinyl)ethoxy]phenoxy]-2-(4-hydroxyphenyl)]benzo[b]thiophene: A Novel, Highly Potent, Selective Estrogen Receptor Modulator, J. Med. Chem., 1997, 40, 1407.

(40) Pamess, J.; Horwitz, S. B., Taxol Binds to Polymerized Tubulin In Vitro, J. Cell Biol. 1981, 91, 479.

(41) Pettit, G. R., Toki, B., Herald, D. L., Verdier-Pinard, P., Boyd, M. R., Hamel, E., Pettit, R. K., Antineoplastic Agents 379. Synthesis of Phenstatin Phosphate, J. Med. Chem., 1998, 41, 1688-1695.

(42) Pettit, G. R., Srirangam, J. K., Barkoczy, J., Williams, M. D., Boyd, M. R., Hamel, E., Pettit, R. K., Hogan F., Bai, R., Chapuis, J. C., McAllister, S. C., Schmidt, J. M., Antineoplastic Agents 365: Dolastatin 10 SAR Probes, Anti-Cancer Drug Des., 1998, 13, 243-277.

(43) Pettit, G. R.; Cragg, G. M.; Singh, S. B., Antineoplastic agents, 122. Constituents of *Combretum caffrum*, J. Nat. Prod 1987, 50, 386.

(44) Pettit, G. R., Kamano, Y., Herald, C. L., Tuinman, A. A., Boettner, F. E., Kizu, H., Schmidt, J. M., Baczynskyj, L., Tomer, K. B., Bontems, R. J., The Isolation and Structure of a Remarkable Marine Animal Antineoplastic Constituent: Dolastatin 10, J. Am. Chem. Soc., 1987, 109, 6883-6885.

(45) Pettit, G. R.; Singh, S. B.; Cragg, G. M., Synthesis of Natural (−) Combretastatin, J. Org. Chem. 1985, 50, 3404.

(46) Pettit, G. R.; Cragg, G. M.; Herald, D. L.; Schmidt, J. M.; Lohavanijaya, P., Isolation and Structure of combretastatin, Can. J. Chem. 1982, 60, 1374.

(47) Pinney et al., Synthesis of a Benzo[b]thiophene-based Vascular Targeting Prodrug and Related Anti-Tubulin Ligands, 220th American Chemical Society, National Meeting, Division of Organic Chemistry, Abstract No. 196, Washington, D.C., Aug. 20-24, 2000.

(48) Pinney, K. G.; Dingeman, K. D.; Bounds, A. D.; Mocharla, V. P.; Pettit, G. R.; Bai, R.; Hamel, E., A New Anti-Tubulin Agent Containing the Benzo[b]thiophene Ring System, Bioorganic and Medicinal Chemistry Letters, 1999, 9, 1081-1086.

(49) Rao, A. V. R.; Sharma, G. V. M.; Bhanu, M. N., Radical Mediated Enantioselective Construction of C-1 to C-9 Segment of Rhizoxin, Tetrahedron Lett. 1992, 33, 3907.

(50) Sawada, T.; Kato, Y.; Kobayashi, H.; Hashimoto, Y.; Watanabe, T.; Sugiyama, Y.; Iwasaki, S., A Fluorescent Probe and a Photoaffinity Labeling Reagent to Study the Binding Site of Maytansine and Rhizoxin on Tubulin, Bioconjugate Chem., 1993, 4, 284.

(51) Safa, A. R.; Hamel, E.; Felsted, R. L., Photoaffinity Labeling of Tubulin Subunits with a Photoactive Analog of Vinblastine, Biochemistry 1987, 26, 97.

(52) Schiff, P. B.; Fant, J.; Horwitz, S. B., Promotion of Microtubule Assembly In Vitro by Taxol, Nature, 1979, 277, 665.

(53) Taylor, S. D.; Chen, M, J,; Dinaut, A. N.; and Batey, R. A., Tetrahedron 1998, 54, 4223-4242.

(54) Tozer, G. M.; Prise, V. E.; Wilson, J.; Locke, R. J.; Vojnovic, B.; Stratford, M. R. L.; Dennis, M. F.; Chaplin, D. J., Combretastatin A-4 Phosphate as a Tumor Vascular-Targeting Agent: Early Effects in Tumors and Normal Tissues. Cancer Res., 1999, 59, 1626.

(55) Von Angerer, E. Tubulin as a target for anticancer drugs. Current opinion in Drug Discovery and Development. 2000, 3, 575-584.

(56) Von Angerer, E.; Prekajac, J.; Strohmeier, J. 2-Phenylchromenes. Relationship between Structure, Estrogen Receptor Affinity, and Mammary Tumor Inhibiting Activity in the Rat. J. Med. Chem. 1984, 27, 1439-1447.

(57) Williams, R. F.; Mumford, C. L.; Williams, G. A.; Floyd, L. J.; Aivaliotis, M. J.; Martinez, R. A.; Robinson, A. K.; Barnes, L. D., A Photoaffinity Derivative of Colchicine: 6-(4'-Azido-2'-nitrophenylamino)hexanoyldeacetylcolchicine. Photolabeling and Location of the Colchicine-binding Site on the alpha-subunit of Tubulin, J. Biol. Chem. 1985, 260, 13794.

(58) Zhang, X.; Smith, C. D., Microtubule Effects of Welwistatin, a Cyanobacterial Indolinone that Circumvents Multiple Drug Resistance, Molecular Pharmacology, 1996, 49, 288.

What is claimed is:

1. A compound of formula (I):

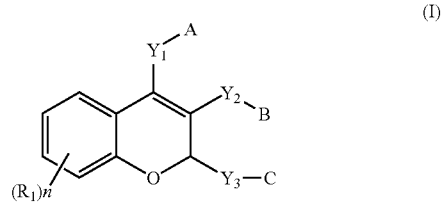

wherein
R$_1$ is independently selected from the group consisting of OH, nitro, lower alkyl, lower alkoxy, phosphate and halogen;
n is 1,2,3 or 4;
Y$_1$ is a covalent bond;
Y$_2$ is —CO—;
Y$_3$ is a covalent bond;
A is H;
C is H; and
B is benzene optionally substituted with —OH, amine, or alkoxy.

2. The compound of claim 1, wherein n is 2.

3. The compound of claim 1, wherein benzene is substituted with 1, 2 or 3 groups.

4. The compound of claim 1, wherein benzene is substituted with alkoxy.

5. The compound of claim 4, wherein alkoxy is methoxy.

6. The compound of claim 1, wherein R$_1$ is lower alkoxy or hydroxyl.

7. The compound of claim 1, wherein R$_1$ is phosphate.

8. The compound of claim 2 wherein R$_1$ is phosphate and alkoxy.

9. The compound of claim 3, wherein benzene is substituted with 3 groups.

10. The compound of claim 9, wherein benzene is substituted with 3 alkoxy groups.

11. The compound of claim 1, wherein the compound is selected from:

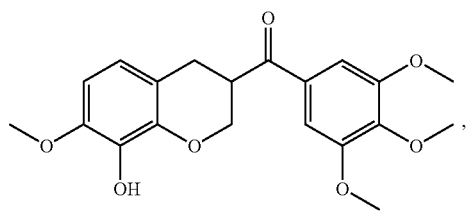

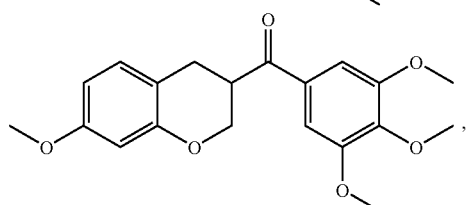

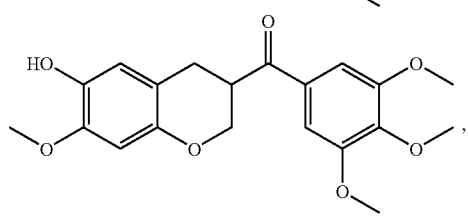

-continued

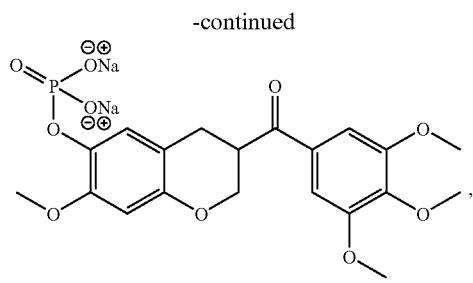,

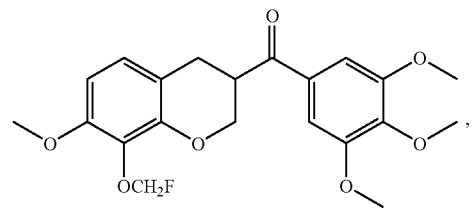,

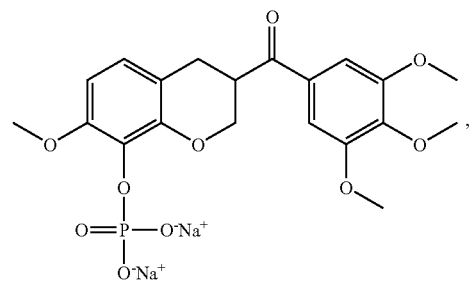,

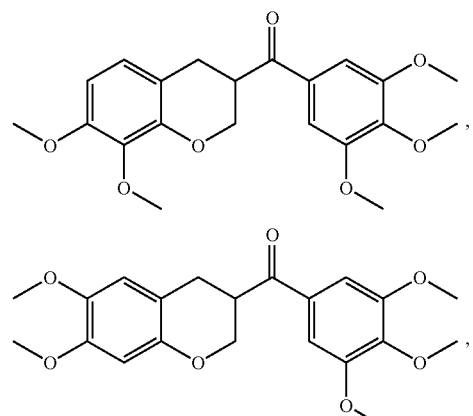,

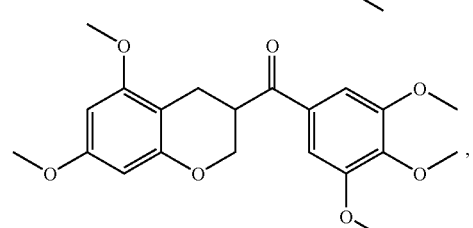,

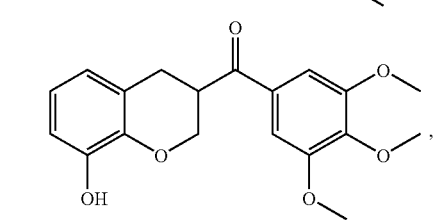,

-continued

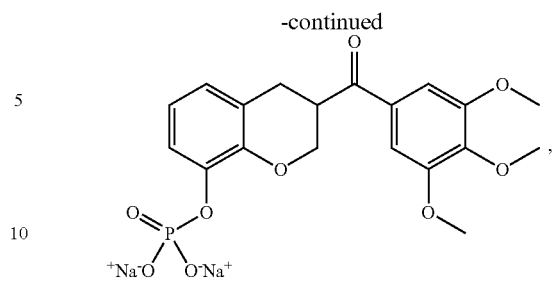,

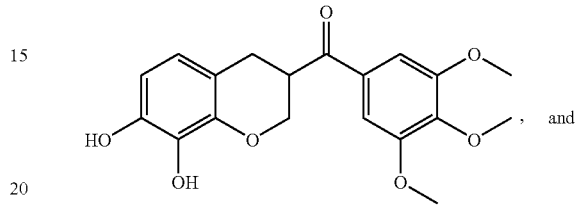, and

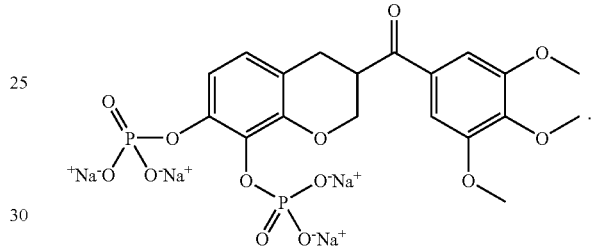.

12. The compound of claim 11, wherein the compound is

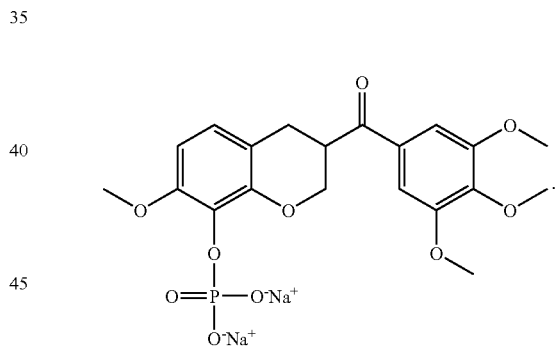.

13. A method for inhibiting tubulin assembly in vitro by contacting a cell with an effective amount of a compound of any one of claim 1.

14. The method of claim 13, wherein said cell is a tumor cell.

15. A method of treating a mammal afflicted with a neoplastic disease by administering to said mammal a therapeutically effective amount of a compound of claim 1.

16. A method for treating cancer by administering to a patient in need thereof, a therapeutically effective amount of a compound claim 1, wherein said cancer is selected from the group consisting of leukemia, lung cancer, colon cancer, thyroid cancer, CNS cancer, melanoma, ovarian cancer, renal cancer, prostate cancer, pancreatic cancer, and breast cancer.

17. A pharmaceutical composition comprising a compound of claim 1 as an active component along with a pharmaceutically acceptable carrier.

18. A method for selectively destroying tumor vasculature in a patient comprising administering an effective amount of a compound of claim 1.

19. A method for selectively reducing blood flow to at least a portion of a neoplastic region, comprising administering an effective amount of a compound of claim 1, wherein substantial necrosis of tissue in the neoplastic region without substantial necrosis of tissue in adjoining regions is effected.

20. The method of claim 19, wherein the effect of reduced tumor blood flow is reversible.

* * * * *